United States Patent
Zhang et al.

(10) Patent No.: US 8,907,153 B2
(45) Date of Patent: Dec. 9, 2014

(54) ADHESIVE PEEL-FORMING FORMULATIONS FOR DERMAL DELIVERY OF DRUGS AND METHODS OF USING THE SAME

(75) Inventors: Jie Zhang, Salt Lake City, UT (US); Kevin S. Warner, West Jordan, UT (US); Michael A. Ashburn, Salt Lake City, UT (US); Larry D. Rigby, Salt Lake City, UT (US); Suyi Niu, Salt Lake City, UT (US)

(73) Assignee: Nuvo Research Inc., Mississauga, Ontario (CA)

( * ) Notice: Subject to any disclaimer, the term of this patent is extended or adjusted under 35 U.S.C. 154(b) by 820 days.

(21) Appl. No.: 11/146,917

(22) Filed: Jun. 6, 2005

(65) Prior Publication Data

US 2005/0276842 A1 Dec. 15, 2005

Related U.S. Application Data

(60) Provisional application No. 60/577,536, filed on Jun. 7, 2004.

(51) Int. Cl.
| A61F 13/00 | (2006.01) |
| A61F 13/02 | (2006.01) |
| A61K 9/70 | (2006.01) |
| A61K 9/14 | (2006.01) |

(52) U.S. Cl.
CPC .................................. *A61K 9/7015* (2013.01)
USPC ............... 602/57; 424/449; 424/487; 602/48; 602/52; 602/54

(58) Field of Classification Search
None
See application file for complete search history.

(56) References Cited

U.S. PATENT DOCUMENTS

| 4,107,161 A | 8/1978 | Augusti |
| 4,430,325 A | 2/1984 | Gaffar et al. |
| 4,645,502 A | 2/1987 | Gale et al. |
| 4,695,465 A | 9/1987 | Kigasawa et al. |
| 4,780,320 A | 10/1988 | Baker |
| 4,956,171 A | 9/1990 | Chang |
| 5,091,171 A | 2/1992 | Yu et al. |
| 5,183,459 A | 2/1993 | Bernard |
| 5,370,879 A | 12/1994 | Masterson et al. |
| 5,378,730 A | 1/1995 | Lee et al. |
| 5,399,355 A | 3/1995 | Riedl et al. |
| 5,460,820 A | 10/1995 | Ebert et al. |
| 5,589,156 A | 12/1996 | Henry |
| 5,658,583 A | 8/1997 | Zhang et al. |
| 5,707,981 A | 1/1998 | Chriki |
| 5,733,572 A | 3/1998 | Unger et al. |
| 5,741,510 A | 4/1998 | Rolf et al. |
| 5,747,022 A | 5/1998 | Slavfcheff |
| 5,747,060 A | 5/1998 | Sackler et al. |
| 5,885,597 A | 3/1999 | Botknecht et al. |
| 5,906,814 A | 5/1999 | Epstein |
| 5,955,502 A | 9/1999 | Hansen et al. |
| 6,036,966 A | 3/2000 | Youssefyeh |
| 6,045,814 A | 4/2000 | Roulier et al. |
| 6,143,794 A | 11/2000 | Chaudhuri et al. |
| 6,207,184 B1 * | 3/2001 | Ikeda et al. .................. 424/448 |
| 6,207,703 B1 | 3/2001 | Ponikau |
| 6,211,250 B1 | 4/2001 | Tomlinson et al. |
| 6,221,915 B1 | 4/2001 | McCleane |
| 6,245,347 B1 | 6/2001 | Zhang et al. |
| 6,290,984 B1 | 9/2001 | Tapolsky et al. |
| 6,290,986 B1 | 9/2001 | Murdock et al. |
| 6,324,424 B1 | 11/2001 | Ledger et al. |
| 6,342,537 B1 | 1/2002 | Thomsen |
| 6,387,383 B1 | 5/2002 | Dow et al. |
| 6,391,869 B1 | 5/2002 | Parks et al. |
| 6,395,955 B1 | 5/2002 | Roe et al. |
| 6,432,415 B1 | 8/2002 | Osborne et al. |
| 6,455,066 B1 | 9/2002 | Fischer et al. |
| 6,495,124 B1 | 12/2002 | Samour |

(Continued)

FOREIGN PATENT DOCUMENTS

| CN | 1426815 | 7/2003 |
| CN | 1739487 A | 3/2006 |
| EP | 0 002 426 | 6/1979 |
| EP | 0 386 960 | 9/1990 |
| EP | 0 455 396 | 11/1991 |
| GB | 1279294 | 6/1972 |
| GB | 2 004 746 | 4/1979 |
| GB | 2028662 A | 3/1980 |
| JP | S46-23277 B | 7/1971 |
| JP | S55-28918 A | 2/1980 |

(Continued)

OTHER PUBLICATIONS

Khazaeinia et al. "A comparison of gastrointestinal permeability induced by diclofenac phospholipid complex with diclofenac acid and its sodium salt" J. Pharmacy and Pharmaceutical Science; 6(3): 352-359, 2003.*

(Continued)

*Primary Examiner* — Jeffrey T Palenik
(74) *Attorney, Agent, or Firm* — Thorpe North & Western LLP

(57) ABSTRACT

The present invention is drawn to adhesive peel-forming formulations for dermal delivery of a drug. The formulation can include a drug, a solvent vehicle, and a peel-forming agent. The solvent vehicle can include a volatile solvent system having one or more volatile solvent, and a non-volatile solvent system having one or more non-volatile solvent, wherein the non-volatile solvent system has a solubility for the drug that is within a window of operable solubility for the drug such that the drug can be delivered at therapeutically effective rates over a sustained period of time. The formulation can have a viscosity suitable for application to a skin surface prior to evaporation of the volatile solvents system. When applied to the skin, the formulation can form a solidified peelable layer after at least a portion of the volatile solvent system is evaporated.

115 Claims, 4 Drawing Sheets

(56) References Cited

U.S. PATENT DOCUMENTS

| | | | |
|---|---|---|---|
| 6,528,086 B2 | 3/2003 | Zhang | |
| 6,562,363 B1 | 5/2003 | Mantelle et al. | |
| 6,635,674 B1 | 10/2003 | Kaneko et al. | |
| 6,653,346 B1 | 11/2003 | Wang et al. | |
| 6,673,363 B2 | 1/2004 | Luo et al. | |
| 6,830,758 B2 | 12/2004 | Nichols et al. | |
| 6,962,691 B1 | 11/2005 | Lulla et al. | |
| 7,198,800 B1 * | 4/2007 | Ko | 424/443 |
| 7,223,418 B2 | 5/2007 | Hidaka et al. | |
| 7,253,155 B2 | 8/2007 | Keith et al. | |
| 2002/0077328 A1 | 6/2002 | Hassan et al. | |
| 2002/0111377 A1 | 8/2002 | Stinchcomb | |
| 2002/0155140 A1 | 10/2002 | Sirinyan et al. | |
| 2003/0018085 A1 | 1/2003 | Raoof et al. | |
| 2003/0049307 A1 | 3/2003 | Gyurik | |
| 2003/0059471 A1 | 3/2003 | Compton et al. | |
| 2003/0091519 A1 | 5/2003 | Zatz et al. | |
| 2003/0096012 A1 | 5/2003 | Besse et al. | |
| 2003/0118655 A1 | 6/2003 | Kundel | |
| 2003/0185915 A1 | 10/2003 | Carlo et al. | |
| 2004/0018241 A1 | 1/2004 | Houze et al. | |
| 2004/0057985 A1 | 3/2004 | Bracht | |
| 2004/0091534 A1 | 5/2004 | Geoghegan et al. | |
| 2004/0141925 A1 | 7/2004 | Bosch et al. | |
| 2004/0143026 A1 | 7/2004 | Shah | |
| 2005/0089539 A1 | 4/2005 | Scholz et al. | |
| 2005/0158274 A1 | 7/2005 | Hunter et al. | |
| 2005/0276842 A1 | 12/2005 | Zhang | |
| 2007/0189977 A1 | 8/2007 | Zhang et al. | |
| 2007/0189978 A1 | 8/2007 | Zhang et al. | |
| 2007/0189980 A1 | 8/2007 | Zhang et al. | |
| 2007/0190124 A1 | 8/2007 | Zhang et al. | |
| 2007/0193453 A1 | 8/2007 | Holcomb et al. | |
| 2007/0196293 A1 | 8/2007 | Zhang et al. | |
| 2007/0196323 A1 | 8/2007 | Zhang et al. | |
| 2007/0196325 A1 | 8/2007 | Zhang et al. | |
| 2007/0196452 A1 | 8/2007 | Zhang et al. | |
| 2007/0196457 A1 | 8/2007 | Zhang et al. | |
| 2007/0196458 A1 | 8/2007 | Zhang et al. | |
| 2007/0196459 A1 | 8/2007 | Zhang et al. | |
| 2007/0280972 A1 | 12/2007 | Zhang et al. | |
| 2008/0019927 A1 | 1/2008 | Zhang et al. | |

FOREIGN PATENT DOCUMENTS

| | | | |
|---|---|---|---|
| JP | S59-039825 A | 3/1984 | |
| JP | 01-110620 | 10/1987 | |
| JP | 01-110623 | 4/1989 | |
| JP | 110620 | 4/1989 | |
| JP | 1110623 | 4/1989 | |
| JP | 2279623 | 11/1990 | |
| JP | 200086440 | 3/2000 | |
| JP | 2002226354 | 8/2002 | |
| WO | WO 92/13529 | 8/1992 | |
| WO | WO 97/29735 | 8/1997 | |
| WO | WO 97/38675 | 10/1997 | |
| WO | WO 99/22717 | 5/1999 | |
| WO | WO 99/49835 | 10/1999 | |
| WO | WO 01/22907 A1 | 4/2001 | |
| WO | WO 01/37890 * | 5/2001 | A61L 26/00 |
| WO | WO 01/43722 A2 | 6/2001 | |
| WO | WO 01/60325 | 8/2001 | |
| WO | WO 02/055023 | 7/2002 | |
| WO | WO 03/059390 | 7/2003 | |
| WO | WO 03/105821 | 12/2003 | |
| WO | WO 2006/097474 | 9/2006 | |
| WO | WO 2007/070643 | 6/2007 | |
| WO | WO 2007/070695 | 6/2007 | |
| WO | WO 2007/070679 A2 | 7/2007 | |
| WO | WO 2011/140236 | 11/2011 | |

OTHER PUBLICATIONS

Handbook of Pharmaceutical Excipients (1988) p. 123 (Glycerin) and p. 241 (Propylene Glycol).*

U.S. Patent Documents—None.*

Non-Patent Documents—None.*

Padilla et al., Topical Medications for Orofacial Neuropathic Pain: A Review, J Am Dent Assoc, vol. 131, No. 2, (2000), pp. 184-195, p. 185-p. 191.

Farber et al., Serotonergic Agents That Activate 5HT2A Receptors Prevent NMDA Antagonist Neurotoxicity, Neuropsychopharmacology, 1998, vol. 18, No. 1, pp. 57-62, p. 60.

Cameo Chemicals Chemical Data Sheet (2 pages) obtained from http://cameochemicals.noaa.gov/chemical/565.

Nortier, Y.L.M. et al. "Preparation and stability testing of a hydrogel for topical analgesia," Jul. 1995, pp. 214-217.

R.D. Wang et al., "Update on ropivacaine" Exper Opin. Pharmacother., 2001, 2(12), pp. 2051-2063.

Dockrell et al., "Imiquimod and resiquimod as novel immunomodulators" J. Antimicrobial Chemother., 2001, 48, pp. 751-755.

An, Na-Mi et al., "Development of a Novel Soft Hydrogel for the Transdermal Delivery of Testosterone," Drug Development and Industrial Pharmacy, 2003, vol. 29, No. 1, pp. 99-105.

Loceryl; "Scary Nails?"; http://www.loceryl.com.au; cited by the Australian associate on Apr. 19, 2013; one page, accessed Jun. 7, 2013.

Wang, et al.; Expert Opinion, Pharmacother, 2001, 2(12) pp. 2051-2063.

Panchagnula; "Feasibility studies of dermal delivery of paclitaxel with binary combination of ethanol and isopropyl myristate: roll of solubility, partitioning and lipid bilayer perturbation"; Farmaco, vol. 60, No. 11-12, Aug. 26, 2005 pp. 894-899.

Kondo; "Enhancement of transdermal delivery by superfluous thermodynamic potential. I. Thermodynamic analysis of nifedipine transport across the lipoidal barrier"; J. Pharmacobiodyn, vol. 10, Apr. 17, 1987, pp. 587-594.

Anonymous; Dermatological and Transdermal Formulations, Chapter 6, 2002 by Marcel Dekker, Inc., pp. 282-284, (case annex, Chapter 6, Formulation Strategies for Modulating Skin Permeation, Davis et al.).

Testosterone-vitamin-d-may-improve- aromatase-inhibitor-joint-problems/bruce jancin; Jan. 13, 2010; 2 pages.

Mackowiak; Clinical Infectious Diseases (2000) vol. 31 (Suppl. 5): p. S154-6.

* cited by examiner

ADHESIVE PEEL-FORMING FORMULATIONS FOR DERMAL DELIVERY OF DRUGS AND METHODS OF USING THE SAME

The present application claims the benefit of U.S. Provisional Application No. 60/577,536, filed on Jun. 7, 2004, which is incorporated herein by reference in its entirety.

FIELD OF THE INVENTION

The present invention relates generally to systems developed for dermal delivery of drugs. More particularly, the present invention relates to adhesive peel-forming formulations having a viscosity suitable for application to a skin surface, and which form a sustained drug-delivering adhesive solidified peelable layer on the skin.

BACKGROUND OF THE INVENTION

Traditional dermal drug delivery systems can generally be classified into two forms: semisolid formulations and dermal patch dosage forms. Semisolid formulations are available in a few different forms, including ointments, creams, pastes, gels, or lotions and are applied topically to the skin. Dermal (including transdermal) patch dosage forms also are available in a few different forms, including matrix patch configurations and liquid reservoir patch configurations. In a matrix patch, the active drug is mixed in an adhesive that is coated on a backing film. The drug-laced adhesive layer is typically directly applied onto the skin and serves both as means for affixing the patch to the skin and as a solvent for the drug. Conversely, in a liquid reservoir patch, the drug is typically incorporated into a solvent system which is held by a thin bag, which can be a thin flexible container. The thin bag can include a permeable or semi-permeable membrane surface that is coated with an adhesive for affixing the membrane to the skin. The membrane is often referred to as a rate limiting membrane (although it may not actually be rate limiting in the delivery process in all cases) and can transfer the drug from within the thin bag to the skin for dermal delivery.

While patches and semisolid formulations are widely used to deliver drugs into and through the skin, they both have significant limitations. For example, most semisolid formulations usually contain solvent(s), such as water and ethanol, which are volatile and thus evaporate shortly after application. The evaporation of such solvents can cause significant decrease or even termination of dermal drug delivery, which may not be desirable in many cases. Additionally, semisolid formulations are often "rubbed into" the skin, which does not necessarily mean the drug formulation is actually delivered into the skin. Instead, this phrase often means that a very thin layer of the drug formulation is applied onto the surface of the skin. Such thin layers of traditional semisolid formulations applied to the skin may not contain sufficient quantity of active drug to achieve sustained delivery over long periods of time. Additionally, traditional semisolid formulations are often subject to unintentional removal due to contact with objects such as clothing, which may compromise the sustained delivery and/or undesirably soil clothing. Drugs present in a semisolid formulation may also be unintentionally delivered to persons who come in contact with a patient undergoing treatment with a topical semisolid formulation.

With respect to matrix patches, in order to be delivered appropriately, a drug should have sufficient solubility in the adhesive, as primarily only dissolved drug contributes to skin permeation driving force. Unfortunately, many drugs have solubility in adhesives that is not high enough to generate sufficient skin permeation driving force. In addition, many ingredients, e.g., liquid solvents and permeation enhancers, which could be used to help dissolve the drug or increase the skin permeability, may not be able to be incorporated into many adhesive matrix systems in sufficient quantities to be effective. For example, at functional levels, most of these materials can tend to adversely alter the wear properties of the adhesive. As such, the selection and allowable quantities of additives, enhancers, excipients, or the like in adhesive-based matrix patches can be limiting. To illustrate, for many drugs, optimal transdermal flux can be achieved when the drug is dissolved in certain liquid solvent systems, but a thin layer of adhesive in a typical matrix patch often cannot hold enough appropriate drug and/or additives to be therapeutically effective. Further, the properties of the adhesives, such as coherence and tackiness, can also be significantly changed by the presence of liquid solvents.

Regarding liquid reservoir patches, even if a drug is compatible with a particular liquid or semisolid solvent system carried by the thin bag of the patch, the solvent system still has to be compatible to the adhesive layer coated on the permeable or semi-permeable membrane; otherwise the drug may be adversely affected by the adhesive layer or the drug/solvent system may reduce the tackiness of the adhesive layer. In addition to these dosage form considerations, reservoir patches are bulkier and usually are more expensive to manufacture than matrix patches.

Another shortcoming of many patches is that they are usually neither sufficiently stretchable nor flexible, as the backing film (in matrix patches) and the thin fluid bag (in reservoir patches) are typically made of relatively non-stretchable materials. If the patch is applied on a skin area that is significantly stretched during body movements, such as a joint, separation between the patch and skin may occur, thereby compromising the delivery of the drug. In addition, a patch present on a skin surface may hinder the expansion of the skin during body movements and cause discomfort. For these additional reasons, patches are not ideal dosage forms for skin areas subject to expansion and stretch during body movements.

In view of the shortcomings of many of the current delivery systems, it would be desirable to provide systems, formulations, and/or methods that can i) provide more sustained drug delivery over long periods of time; ii) are not vulnerable to unintentional removal by contact with clothing, other objects, or people for the duration of the application time; iii) can be applied to a skin area subject to stretching and expansion without causing discomfort or poor contact to skin; and/or iv) can be easily removed after application and use.

SUMMARY OF THE INVENTION

It has been recognized that it would be advantageous to provide dermal delivery formulations, systems, and/or methods in the form of adhesive peel-forming compositions or formulations having a viscosity suitable for application to the skin surface and which form a drug-delivering solidified peelable layer on the skin that is easily peelable or removable after use. In accordance with this, an adhesive peel-forming formulation for dermal delivery of a drug can comprise a drug, a solvent vehicle, and a peel-forming agent. The solvent vehicle can comprise a volatile solvent system having one or more volatile solvent(s) and a non-volatile solvent system having one or more non-volatile solvent(s), wherein the non-volatile solvent system provides a window of operable solubility for the drug such that the drug can be delivered in therapeutically effective amounts over a period of time, even after most of the volatile solvent(s) is (are) evaporated. The formulation can have viscosity suitable for application to the skin surface prior to evaporation of at least one volatile solvent, and can further be configured such that when applied to the skin surface, the formulation forms a solidified peelable layer after at least a portion of the volatile solvent(s) is (are) evaporated.

In an alternative embodiment, a method of dermally delivering a drug to a subject can comprise applying an adhesive peel-forming formulation to a skin surface of the subject, dermally delivering the drug from the solidified peelable layer over a period of time and at desired rates, and removing the solidified peelable layer from the skin after a period of time has elapsed or the desired quantity of the drug has been delivered. The adhesive peelable formulation can include a drug, a solvent vehicle, and a peel-forming agent. The solvent vehicle can comprise a volatile solvent system having one or more volatile solvent(s) and a non-volatile solvent system having one or more non-volatile solvent(s), wherein the non-volatile solvent system has a solubility for the drug that is within a window of operable solubility for the drug such that the drug can be delivered in therapeutically effective amounts over a period of time, even after most of the volatile solvent(s) is (are) evaporated. The formulation can have a viscosity suitable for application to a skin surface prior to evaporation of the volatile solvent(s). When the formulation is applied to the skin surface, the formulation can form a solidified peelable layer after at least a portion of the volatile solvent system evaporated.

In another embodiment, a method of preparing an adhesive peelable formulation for dermal drug delivery can comprise steps of selecting a drug suitable for dermal delivery; selecting a non-volatile solvent system consisting essentially of one non-volatile solvent that has a solubility with respect to the drug within a window of operable solubility; and formulating the drug and the non-volatile solvent into an adhesive peel-forming formulation. The adhesive peel-forming formulation can include a peel-forming agent and a volatile solvent system including at least one volatile solvent. The adhesive peel-forming formulation can have a viscosity suitable for application to a skin surface prior to evaporation of the volatile solvent system, and can be applied to the skin surface where it forms a solidified peelable layer after at least a portion of the volatile solvent system is evaporated. In this embodiment, the drug continues to be delivered at a therapeutically effective amount after the volatile solvent system is substantially evaporated.

In another embodiment, a method of preparing an adhesive peel-forming formulation for dermal drug delivery can comprise steps of selecting a drug suitable for dermal delivery; forming a non-volatile solvent system by selecting at least two non-volatile solvents according to a ratio that positions the solubility of the drug within a window of operable solubility with respect to the non-volatile solvent system; and formulating the drug and the non-volatile solvent system into an adhesive peel-forming formulation. The adhesive peel-forming formulation can include a peel-forming agent and a volatile solvent system including at least one volatile solvent. The adhesive peel-forming formulation can also have a viscosity suitable for application to a skin surface prior to evaporation of the volatile solvent system, and can be applied to the skin surface where it forms a solidified peelable layer after at least a portion of the volatile solvent system is evaporated. The drug can continue to be delivered at a therapeutically effective amount after the volatile solvent system is substantially evaporated.

In still another embodiment, a solidified peelable layer for delivering a drug can comprise a drug, a non-volatile solvent system, and a peel-forming agent. The non-volatile solvent system can include one or more non-volatile solvent(s), and can provide a window of operable solubility for the drug such that the drug can be delivered in a therapeutically effective amount for at least 2 hours. Further, the peelable layer can be stretched in at least one direction by 10% without breaking, cracking, or separation from a skin surface to which the solidified peelable layer is applied.

In still another embodiment, an adhesive peel-forming formulation for dermal delivery of a drug can comprise a drug, a peel-forming agent, and a solvent vehicle. The solvent vehicle can include a volatile solvent system including one or more volatile solvent, a non-volatile solvent system including one or more non-volatile solvent. After the adhesive peel-forming formulation is applied to a skin surface, the adhesive peel-forming formulation forms a solidified peelable layer having a contact surface having a first area dimension. The solidified peelable layer can be stretchable such that the first area dimension is capable of being stretched to a second area dimension that is 10% larger than the first area dimension without cracking, breaking, and/or separating from a skin surface to which the peel-forming formulation is applied. Further, after the formation of the solidified peelable layer and after the volatile solvent system is substantially evaporated, the drug continues to be delivered in therapeutically effective amounts.

Additional features and advantages of the invention will be apparent from the following detailed description and figures which illustrate, by way of example, features of the invention.

DETAILED DESCRIPTION OF THE PREFERRED EMBODIMENTS

Figure 1:
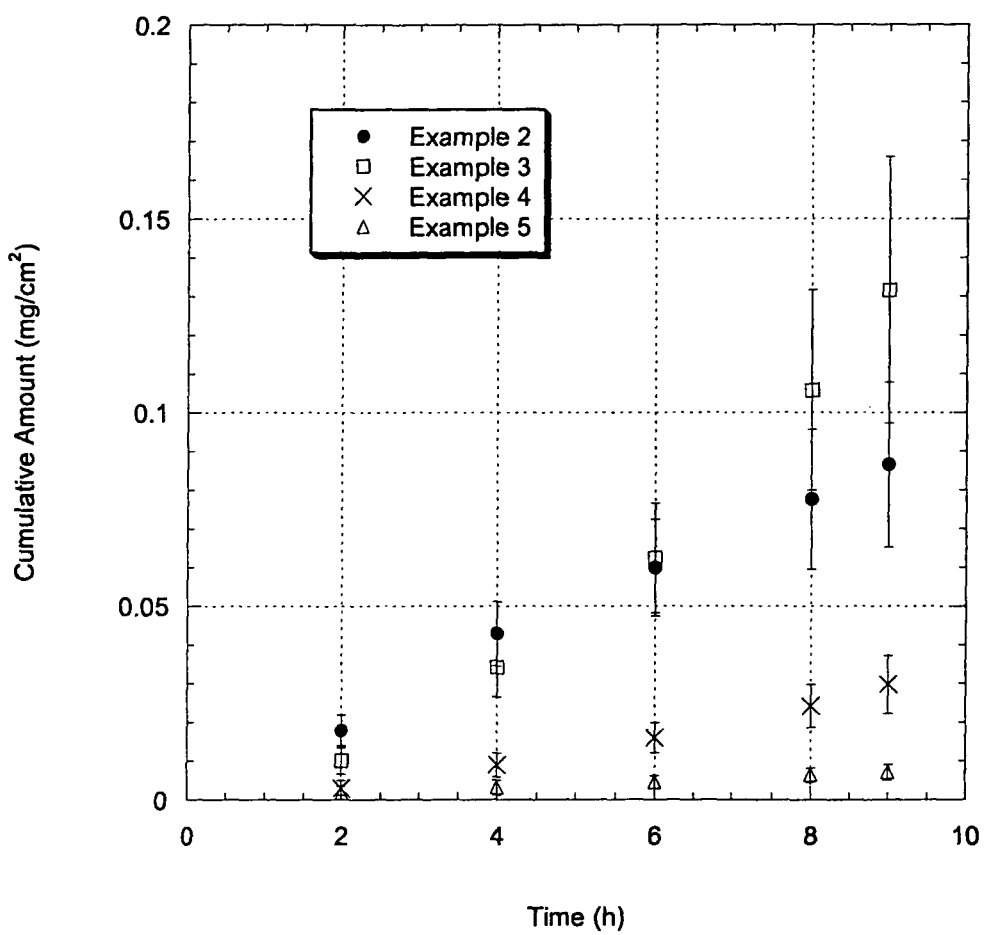
FIGS. 1-4 are graphical representations of cumulative amount of a drug delivered across a biological membrane in vitro over time from four separate solidified adhesive formulations in accordance with embodiments of the present invention.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a drug" includes reference to one or more of such compositions.

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

"Skin" is defined to include human skin, finger and toe nail surfaces, and mucosal surfaces that are usually at least partially exposed to air such as lips, genital and anal mucosa, and nasal and oral mucosa.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

The phrase "effective amount," "therapeutically effective amount," or "therapeutically effective rate(s)" of a drug refers to a non-toxic, but sufficient amount or delivery rates of the drug, to achieve therapeutic results in treating a condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The phrases "dermal drug delivery" or "dermal delivery of drugs" shall include both transdermal and topical drug delivery, and shall mean the delivery of drug(s) to, through, or into the skin. When transdermally delivering the drug, skin, tissues just under the skin, regional tissues or organs under the skin, systemic circulation, and/or the central nervous system, for example, can be targeted.

The term "drug(s)" refers to any bioactive agent that is applied to, into, or through the skin which is applied for achieving a therapeutic affect. This includes compositions that are traditionally identified as drugs, as well other bioactive agents that are not always considered to be "drugs" in the classic sense, e.g., peroxides, humectants, emollients, etc., but which can provide a therapeutic effect for certain conditions.

The term "window of operable solubility" refers to a solubility range provided by a non-volatile solvent system for a selected drug. A drug solubilized in a non-volatile solvent system with a solubility for the drug within the window of operable solubility can provide acceptable skin permeation driving force, including optimal or near optimal dermal permeation driving force. The appropriate selection or formulation of the non-volatile solvent system in the adhesive peelable formulations of the present invention is used to make sure that the solubility of the drug is within the "window of operable solubility" which leads to desired dermal or transdermal delivery rates. In other words, in order to achieve acceptable dermal delivery or transdermal flux/driving force of a drug to or into a skin surface, drug solubility in the non-volatile solvent system, which is the maximum amount of the drug that can be dissolved in a unit volume of the solvent system, should be within this window of operable solubility, e.g., not overly soluble nor too poorly soluble.

Generally, transdermal permeation driving force for a drug typically increases by increasing drug concentration in a non-volatile solvent system, until the solution is saturated. Conversely, for a given drug concentration that is fully dissolved, the driving force usually decreases with increasing solubility or decreasing saturation. This can be explained in accordance with certain physical chemistry principles, wherein a drug tends to stay in a solution in which it has better solubility. Stated another way, where a drug has good affinity with a solution (as reflected by high solubility), the drug will tend to stay in solution rather than venture outside of the solution and permeate into the skin. Thus, low transdermal flux can be a result of not only insufficient drug solubility in a non-volatile solvent system, but also can be a result of the drug being too "comfortable" (high drug-non volatile solvent affinity) within the non-volatile solvent system. Therefore, to achieve acceptable drug delivery, there exists a window of operable solubility for a given drug, and the solubility of the drug in the non-volatile solvent system should be within this window in order to provide sufficient or desired (which often, but not always means close to maximum) transdermal driving force for the drug. This window of operable solubility is typically individualized for each drug. However, it is usually in the range of 0.01 wt % to 40 wt % of the adhesive peelable formulation as a whole, and for many drugs, in the range of 0.5 wt % to 20 wt %.

To illustrate this principle more fully, one can consider two formulations, one having a non-volatile solvent system that is capable of dissolving 100 mg of a drug in each mL of solvent (solubility is 100 mg/mL) and another having a non-volatile solvent system with the solubility for the same drug at 6 mg/mL. If 5 mg of drug are placed in 1 mL of each system, both would fully solubilize the drug, but the driving force of the drug in the 6 mg/mL non-volatile solvent system would typically be much greater than the driving force provided by 100 mg/mL non-volatile solvent system. In other words, even though the drug is fully dissolved in both systems, the drug would have better affinity with the 100 mg/mL system and would thus provide a lower driving force for dermal permeation.

This is also supported by thermodynamics and diffusion concepts, where the "window of operable solubility" reflects a range of drug (solute) activities in a non-volatile solution that is needed for delivering sufficient flux or amount of the drug across the skin or mucosal membrane.

More quantitatively, the flux of permeation, defined as quantity of drug permeated across a unit area of skin (typically one square centimeter) over a unit length of time (typically one hour), is given by:

$$J = PC \qquad (1)$$

where C is the concentration of dissolved drug and P is the permeability coefficient of the drug across the skin or mucosal membrane, and is independent of drug concentration. P is dependent of the drug and the formulation, but, based on all data that the inventors are aware of, is usually not higher than $10^{-5}$ cm/sec for even a well optimized transdermal drug delivery system.

Equation (1) and the observed cap of P suggest that sufficient flux cannot be achieved if the drug concentration is too low. Since the drug concentration is capped by the solubility of the drug in the formulation, this means the formulation has to have certain solubility for the drug in order to have sufficient flux.

Thus, Equations (1) supports the concept that that there exists a range of solubility outside of which the formulation will not yield desired or operable dermal permeation driving force. The appropriate selection and/or formulation of the non-volatile solvent system in the peel formulations is utilized in this invention to assure that the solubility is within this "window of operable solubility" which leads to the desired transdermal properties.

The phrase "substantially constant" when referring to "sustained delivery" of drug can be defined in terms of either an in vitro permeability across human or hairless mouse skin or epidermis, or by a data collected from a pool of 12 or more human subjects, wherein the drop in mean drug delivery rate over a specified period of time (2 hours or longer) is not more than 50% from a peak drug delivery rate. Thus, compositions that are delivered at a "substantially constant" rate include formulations that deliver a drug at substantially constant and therapeutically significant rates for an sustained period of time, e.g., 2 hours, 4 hours, 8 hours, 12 hours, 24 hours, etc. The use of non-volatile solvent systems having a window of operable solubility as defined previously can achieve this sustained delivery at therapeutically significant rates over sustained period of time.

"Volatile solvent system" can be a single solvent or a mixture of solvents that are volatile, including water and solvents that are more volatile than water.

"Non-volatile solvent system" can be a single solvent or mixture of solvents that are less volatile than water. Most of the non-volatile solvent system should remain in the solidified peelable layer after volatile solvent system evaporation for a time sufficient to dermally delivery a given drug to, into, or through the skin of a subject at a sufficient flux for a period of time to provide a therapeutic effect. In some embodiments, in order to obtain desired solubility for an active drug and/or compatibility with peel-forming agents or other ingredients of the formulation, a mixture of two or more non-volatile solvents can be used to form the non-volatile solvent system.

The term "solvent vehicle" describes compositions that include both a volatile solvent system and non-volatile solvent system. The volatile solvent system is chosen so as to evaporate from the adhesive peelable formulation quickly to form a solidified peelable layer, and the non-volatile solvent system is formulated or chosen to substantially remain with the solidified peelable layer after volatile solvent system evaporation to achieve continued delivery of the drug. Typically, the drug can be partially or completely dissolved in the solvent vehicle or formulation as a whole. Likewise, the drug can also be partially or completely solubilizable in the non-volatile solvent system once the volatile solvent system is evaporated. Formulations in which the drug is only partially dissolved in the non-volatile solvent system after the evaporation of the volatile solvent system have the potential to maintain longer duration of sustained delivery, as the undissolved drug can dissolve into the non-volatile solvent system as the dissolved drug is being depleted from the solidified peelable layer during drug delivery.

"Adhesive peelable formulation" or "adhesive peel-forming formulation" refers to a composition that has a viscosity suitable for application to a skin surface prior to evaporation of its volatile solvent(s), and which can become a solidified peelable layer (or a peel) after evaporation of at least a portion of the volatile solvent(s).

The term "drying time" refers to the time it takes for the formulation to form a non-messy solidified surface after application on skin under standard skin and ambient conditions, and with standard testing procedure. "Standard skin" or "normal skin" is defined as dry, healthy human skin with a surface temperature of between 32° C. to 36° C.; standard ambient conditions are defined from 20° C. to 25° C. and from 20% to 80% relative humidity. The standard testing procedure is as follows. To standard skin at standard ambient conditions is applied an approximately 0.2 mm layer of the adhesive peel-forming formulation and the drying time is measured. The drying time is defined as the time it takes for the formulation to form a non-messy surface such that the formulation does not lose mass by adhesion to a piece of 100% cotton cloth pressed onto the formulation surface with a pressure of between 5 and 10 g/cm$^2$ for 5 seconds.

When a composition is said to have a viscosity "suitable for application" to a skin surface, this means the composition has a viscosity that is high enough so that the composition does not substantially run off the skin after being applied to skin, but also has a low enough viscosity so that it can be easily spread onto the skin. A viscosity range that meets this definition can range from 100 cP to 3,000,000 cP (centipoises), and more preferably from 1,000 cP to 1,000,000 cP.

"Solidified peelable layer" or "peel" describes the solidified or dried layer of an adhesive peel-forming formulation after at least a portion of the volatile solvent system has evaporated. The peel remains adhered to the skin, and is preferably capable of maintaining good contact with the patient's skin for substantially the entire duration of application under normal skin and ambient conditions. The peel also exhibits sufficient tensile strength so that it can be peeled off the skin at the end of the application in one piece or several large pieces (as opposed to a layer with weak tensile strength that breaks into many small pieces or crumbles when removed from the skin).

With these definitions in mind, the present invention is related to novel formulations that are typically in the initial form of semi-solids (including creams, gels, pastes, ointments, and other viscous liquids), which can be easily applied onto the skin as a layer, and can quickly (from 15 seconds to 4 minutes under normal skin and ambient conditions) to moderately quickly (from 4 to 15 minutes under normal skin and ambient conditions) change into a solidified peelable layer or peel, e.g., a coherent and soft solid layer, for drug delivery. A solidified peelable layer or peel thus formed is capable of delivering drug to the skin, into the skin, across the skin, etc., at substantially constant rates, over an sustained period of time, e.g., hours to tens of hours, so that most of the active drug is delivered after the solidified peelable layer is formed. Additionally, the solidified peelable layer typically adheres to the skin, but has a solidified, minimally-adhering, outer surface which is formed relatively soon after application and which does not substantially transfer to or otherwise soil clothing or other objects that a subject is wearing or that the peel may inadvertently contact. The solidified peelable layer can also be formulated such that it is highly flexible and stretchable, and thus capable of maintaining good contact with a skin surface, even if the skin is stretched during body movement, such as at a knee, finger, elbow, or other joints.

In selecting the various components that can be used, e.g., drug, solvent vehicle of volatile solvent system and non-volatile solvent system, peel-forming agent(s), etc., various considerations can occur. For example, the volatile solvent system can be selected from pharmaceutically or cosmetically acceptable solvents known in the art. Examples of such volatile solvents include water, ethanol, propyl alcohol, ethyl acetate, acetone, or the like. Additionally, these volatile solvents should be chosen to be compatible with the rest of the formulation. It is desirable to use an appropriate weight percentage of the volatile solvent(s) in the formulation. Too much of the volatile solvent system prolongs the drying time. Too little of the volatile solvent system can make it difficult to spread the formulation on the skin. For most formulations, the weight percentage of the volatile solvent(s) can be from about 2 wt % to about 50 wt %, and more preferably from about 4 wt % to about 30 wt %.

The non-volatile solvent system can also be chosen or formulated to be compatible with the peel-forming agent, the drug, the volatile solvent, and any other ingredients that may be present. For example, the peel-forming agent can be chosen so that it is dispersible or soluble in the non-volatile solvent system. Most non-volatile solvent systems and solvent vehicles as a whole will be formulated appropriately after experimentation. For instance, certain drugs have good solubility in poly ethylene glycol (PEG) having a molecular weight of 400 (PEG 400, non-volatile solvent) but poor solubility in glycerol (non-volatile solvent) and water (volatile solvent). However, PEG 400 cannot effectively dissolve poly vinyl alcohol (PVA), and thus, is not very compatible alone with PVA, a peel-forming agent. In order to dissolve sufficient amount of an active drug and use PVA as a peel-forming agent at the same time, a non-solvent system including PEG 400 and glycerol (compatible with PVA) in an appropriate ratio can be formulated, achieving a compatibility compromise. As a further example of compatibility, non-volatile solvent/film forming agent incompatibility is observed when Span 20 is formulated into a peel formulation containing PVA. With this combination, Span 20 can separate out of the formulation and form an oily layer on the surface of the peel. Thus, appropriate film forming agent/non-volatile solvent selections are desirable in developing a viable formulation and compatible combinations.

Non-volatile solvent(s) that can be used alone or in combination to form non-volatile solvent systems can be selected from a variety of pharmaceutically acceptable liquids, including but not limited to glycerol, poly ethylene glycol having a weight average molecular weight from about 200 MW to 800 MW, mineral oil, petrolatum, castor oil, essential oils such as eugenol, menthol, cineole, or rose oil, n-methyl pyrrolidone, vegetable oils, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, oleic acid, dimethylsulfoxide (DMSO), fatty alcohol, isopropyl myristate (IPM), triacetin, ethyl oleate, isostearic acid, medium chain fatty acid and other fatty acids, and mixtures thereof. In addition to these and other considerations, the non-volatile solvent system can also serve as plasticizer in the adhesive peelable formulation so that when the solidified peelable layer is formed, the layer is flexible, stretchable, and/or otherwise "skin friendly."

Certain volatile and/or nonvolatile solvent(s) that are irritating to the skin may be desirable to use to achieve the desired solubility and/or permeability of the drug. It is also desirable to add compounds that are both capable of preventing or reducing skin irritation and are compatible with the formulation. For example, in a formulation where the volatile solvent is capable of irritating the skin, it would be helpful to use a non-volatile solvent that is capable of reducing skin irritation. Examples of solvents that are known to be capable of preventing or reducing skin irritation include, but are not limited to, glycerin, honey, and propylene glycol.

The selection of the peel-forming agent can also be carried out in consideration of the other components present in the adhesive peelable formulation. The peel-forming agent can be selected or formulated to be compatible to the drug and the solvent vehicle (including the volatile solvent(s) and the non-volatile solvent system), as well as provide desired physical properties to the solidified peelable layer once it is formed. Depending on the drug, solvent vehicle, and/or other components that may be present, the peel-forming agent can be selected from a variety of agents, including but not limited to polyvinyl alcohol, polyvinyl pyrrolidone, carrageenin, gelatin, dextrin, gelatin, guar gum, polyethylene oxide, starch, xantham gum, cellulose derivatives including hydroxyethylcellulose, ethylcellulose, carboxymethylcellulose, hydroxypropylcellulose, polyvinyl alcohol-polyethylene glycol copolymers and methyacrylic acid-ethyl acrylate copolymers such as BASF's Kollicoat polymers, methacrylic acid and methacrylate based polymers such as poly(methacrylic acid) copolymers and methylmethacrylate copolymers, including Rohm & Haas' Eudragit polymers, e.g., Eudragit E, Eudragit RL, Eudragit RS, and polymers of the same or similar chemical nature but are generic or under different brand names or chemical names, and mixtures thereof. Many other film forming polymers may also be suitable as the peel-forming agent, depending on the solvent vehicle components, the drug, and the specific functional requirements of the given formulation.

The non-volatile solvent system and the peel-forming agent should be compatible with each other. Compatibility is defined as i) the peel-forming agent does not substantially negatively influence the function of the non-volatile solvent system; ii) the peel-forming agent can hold the non-volatile solvent system in the solidified peelable layer so that substantially no non-volatile solvent oozes out of the layer, and iii) the solidified peelable layer formed with the selected non-volatile solvent system and the peel-forming agent has acceptable flexibility, rigidity, tensile strength, elasticity, and adhesiveness. The weight ratio of the non-volatile solvent system to the peel-forming agent can be from about 0.01:1 to about 2:1. In another aspect, the ratio between the non-volatile solvent system and the peel-forming agent can be from about 0.2:1 to about 1.2:1.

To provide some practical parameters, typically, concentrations of active drugs in topical formulations rarely exceed 10 wt % (by weight of active drug in weight of total formulation). If on embodiment, if the non-volatile solvent system of a formulation makes up 30 wt % of the total formulation weight, this means the concentration of the active drug in the non-volatile solvent system is about 25 wt %. In such a formulation, the permeation driving force will be significantly reduced if the solubility of the non-volatile solvent system for the drug is much higher than 25 wt %. The maximum drug concentrations in many physically and commercially viable products are significantly less than 10 wt %, which in turn means the upper limits of the window of operable solubility are significantly lower for those systems, more likely in the 1 wt % to 10 wt % range.

The thickness of the formulation layer applied on the skin should also be appropriate for a given formulation and desired drug delivery considerations. If the layer is too thin, the amount of the drug may not be sufficient to support sustained delivery over the desired length of time. If the layer is too thick, it may take too long to form a non-messy outer surface of the solidified peelable layer. If the drug is very potent and the peel has very high tensile strength, a layer as thin as 0.01 mm may be sufficient. If the drug has rather low potency and the peel has low tensile strength, a layer as thick as 2-3 mm maybe needed. Thus, for most drugs and formulations, the appropriate thickness can be from about 0.01 mm to about 3 mm, but more typically, from about 0.05 mm to about 1 mm.

The flexibility and stretchability of a solidified peelable layer, or peel, can be desirable in some applications. For instance, certain non-steroidal anti-inflammatory agents (NSAIDs) can be applied directly over joints and muscles for transdermal delivery into joints and muscles. However, skin areas over joints and certain muscle groups are often significantly stretched during body movements. Such movement prevents non-stretchable patches from maintaining good skin contact. Lotions, ointments, creams, gels, pastes, or the like also may not be suitable for use for the reasons cited above. As such, in transdermal delivery of NSAIDs into joints and/or muscles, the peel-forming formulations of the present invention can offer unique advantages and benefits. It should be pointed out that although good stretchability can be desirable in some applications. The peel-forming formulations of the present invention do not always need to be stretchable, as certain applications of the present invention do not necessarily benefit from this property. For instance, if the formulation is applied on a small facial area overnight for treating acne, a patient would experience minimal discomfort and formulation-skin separation even if the peel is not stretchable, as facial skin usually is not stretched very much during a sleep cycle.

A further feature of a formulation is related to the drying time. If a formulation dries too quickly, the user may not have sufficient time to spread the formulation into a thin layer on the skin surface before the formulation is solidified, leading to poor skin contact. If the formulation dries too slowly, the patient may have to wait a long time before resuming normal activities (e.g. putting clothing on) that may remove un-solidified formulation. Thus, it is desirable for the drying time to be longer than about 15 seconds but shorter than about 15 minutes, and preferably from about 0.5 minutes to about 4 minutes.

Other benefits of the solidified peelable layers of the present invention include the presence of a physical barrier that can be formed by the material itself. For instance, local anesthetic agents and other agents such as clonidine may be delivered topically for treating pain related to neuropathy, such as diabetic neuropathic pain. Since many of such patients feel tremendous pain, even when their skin area is only gently touched, the physical barrier of the solidified peelable layer can prevent or minimize pain caused by accidental contact with objects or others.

These and other advantage can be summarized as follows. The solidified peelable layers of the present invention can be prepared in an initial form that is easy to apply as a semisolid dosage form. Additionally, upon volatile solvent system evaporation, the dosage form is relatively thick and can contain much more active drug than a typical layer of traditional cream, gel, lotion, ointment, paste, etc., and further, is not as subject to unintentional removal. After the evaporation of the volatile solvent(s) and the formation of the solidified peelable layer, the drug in the remaining non-volatile solvent system whose solubility with respect to the drug is within the window of operable solubility for the drug can provide desired delivery rates of the drug over sustained periods of time. Further, as the solidified peelable layer remains adhesive and is peelable, easy removal of the solidified peelable layer can occur, usually without the aid of a solvent or surfactant. In some embodiments, the adhesion to skin and elasticity of the material is such that the solidified peelable layer will not separate from the skin upon skin stretching at highly stretchable skin areas, such as over joints and muscles. For example, in one embodiment, the solidified peelable layer can be stretched to 10% or greater in one direction without cracking, breaking, and/or separating form a skin surface to which the peelable layer is applied. In another embodiment, the area of the solidified peelable layer that contacts the skin can be stretched to a 10% increase in area without cracking, breaking, and/or separating form a skin surface to which the peelable layer is applied. Still further, the solidified peelable layer can be configured to advantageously deliver drug and protect sensitive skin areas without cracking or breaking.

Specific examples of applications that can benefit from the systems, formulations, and methods of the present invention are as follows. In one embodiment, a solidified peelable layer including bupivacaine, lidocaine, or ropivacaine, can be formulated for treating diabetic and post herpetic neuralgia. Alternatively, dibucanine and an alpha-2 agonist such as clonidine can be formulated in a peel for treating the same disease. In another embodiment, retinoic acid and benzoyl peroxide can be combined in a solidified peelable layer for treating acne, or alternatively, 1 wt % clindamycin and 5 wt % benzoyl peroxide can be combined in a peel for treating acne. In another embodiment, a retinol peel-forming formulation (OTC) can be prepared for treating wrinkles, or a lidocain peel-forming formulation can be prepared for treating back pain.

Additional applications include delivering drugs for treating certain skin conditions, e.g., psoriasis, skin cancer, etc., particularly those that occur over joints or muscles where a transdermal patch may not be practical. For example, peel-forming formulations containing imiquimod can be formulated for treating skin cancer, common and genital warts, and actinic keratosis. Peel-forming formulations containing antiviral drugs such as acyclovir, penciclovir, famciclovir, valacyclovir, steroids, behenyl alcohol can be formulated for treating herpes viral infections such as cold sores on the face and genital areas. Peel-forming formulations containing non-steroidal anti-inflammatory drugs (NSAIDs), capsaicin, alpha-2 agonists, and/or nerve growth factors can be formulated for treating soft tissue injury and muscle-skeletal pains such as joint and back pain of various causes. As discussed above, patches over these skin areas typically do not have good contact over sustained period of time, especially for a physically active patient, and may cause discomfort. Likewise, traditional semisolid formulations such as creams, lotions, ointments, etc., may prematurely stop the delivery of a drug due to the evaporation of solvent and/or unintentional removal of the formulation. The solidified adhesive formulations of the present invention address the shortcomings of both of these types of delivery systems.

One embodiment entails a peel containing a drug from the class of alpha-2 antagonists which is applied topically to treat neuropathic pain. The alpha-2 agonist is gradually released from the formulation to provide pain relief over a sustained period of time. The formulation can become a coherent, soft solid after 2-4 minutes and remains adhered to the body surface for the length of its application. It is easily removed after drying without leaving residual formulation on the skin surface.

Another embodiment involves a peel formulation containing capsaicin which is applied topically to treat neuropathic pain. The capsaicin is gradually released from the formulation for treating this pain over a sustained period of time. The formulation can become a coherent, soft solid after 2-4 minutes and remains adhered to the body surface for the length of its-application. It is easily removed any time after drying without leaving residual formulation on the skin surface.

Still another embodiment involves a peel formulation containing a drug selected from the NSAID class, such as piroxicam, diclofenac, indomethacin, which is applied topically to treat symptoms of back pain, muscle tension, or myofascial pain or a combination thereof. The NSAID is gradually released from the formulation to provide pain relief over a sustained period of time. The formulation can become a coherent, soft solid after 2-4 minutes and remains adhered to the body surface for the length of its application. It is easily removed any time after drying without leaving residual formulation on the skin surface.

A further embodiment involves a peel formulation containing at least one alpha-2 agonist drug and at least one local anesthetic drug which is applied topically to treat neuropathic pain. The drugs are gradually released from the formulation to provide pain relief over a sustained period of time. The formulation can become a coherent, soft solid after 2-4 minutes and remains adhered to the body surface for the length of its application. It is easily removed any time after drying without leaving residual formulation on the skin surface.

A similar embodiment can include a peel formulation containing drugs capsaicin and a local anesthetic drug which is applied topically to the skin to provide pain relief. Another embodiment can include a peel formulation containing the combination of a local anesthetic and a NSAID. In both of the above embodiments the drugs are gradually released from the formulation to provide pain relief over an sustained period of time. The formulation can become a coherent, soft solid after 2-4 minutes and remains adhered to the body surface for the length of its application. It is easily removed any time after drying without leaving residual formulation on the skin surface.

In another embodiment, peel-forming formulations for the delivery of drugs that treat the causes or symptoms of diseases involving joints and muscles can also benefit from the systems, formulations, and methods of the present invention. Such diseases that may be applicable include, but not limited to, osteoarthritis (OA), rheumatoid arthritis (RA), joint and skeletal pain of various other causes, myofascial pain, muscular pain, and sports injuries. Drugs or drug classes that can be used for such applications include, but are not limited to, non-steroidal anti-inflammatory drugs (NSAIDs) such as ketoprofen and diclofanec, COX-2 selective NSAIDs and agents, COX-3 selective NSAIDs and agents, local anesthetics such as lidocaine, bupivacaine, ropivacaine, and tetracaine, steroids such as dexamethasone.

Delivering drugs for the treatment of acne and other skin conditions can also benefit from principles of the present invention, especially when delivering drugs having low skin permeability. Currently, topical retinoids, peroxides, and antibiotics for treating acne are mostly applied as traditional semisolid gels or creams. However, due to the shortcomings as described above, sustained delivery over many hours is unlikely. For example, clindamycin, benzoyl peroxide, and erythromycin may be efficacious only if sufficient quantities are delivered into hair follicles. However, a semisolid formulation, such as the popular acne medicine benzaclin gel, typically loses most of its solvent (water in the case of benzaclin) within a few minutes after the application, which likely substantially compromises the sustained delivery of the drug. The formulations of the present invention typically do not have this limitation.

In another embodiment, the delivery of drugs for treating neuropathic pain can also benefit from the methods, systems, and formulations of the present invention. A patch containing a local anesthetic agent, such as Lidoderm™, is widely used for treating neuropathic pain, such as pain caused by postherpetic neuralgia and diabetes induced neuropathic pain. Due to the limitations of the patch as discussed above, the solidified peelable layers prepared in accordance with the present invention provide some unique benefits, as well as provide a potentially less expensive alternative to the use of a patch. Possible drugs delivered for such applications include, but are not limited to, local anesthetics such as lidocaine, prilocaine, tetracaine, bupivicaine, etidocaine; and other drugs including capsaicin and alpha-2 agonists such as clonidine.

In yet another embodiment, the delivery of medication for treating warts and other skin conditions would also benefit from long periods of sustained drug delivery. Such drugs that can be used in the formulations of the present invention include, but are not limited to, salicylic acid and imiquimod.

In another embodiment, the delivery of natural substances and nutrients such as retinol (Vitamin A) and humectants or emollients to the skin for cosmetic purposes can also benefit from the systems, formulations, and methods of the present invention.

A further embodiment involves the delivery of anti-fungal agents such as ciclopirox, imidazoles, miconazole, clotrimazole, econazole, ketoconazole, oxiconazole, sulconazole and allylamine derivatives such as butenafine, naftifine, and terbinafine, to the skin so as to eliminate or alleviate various fungal disorders. Delivery can be accomplished through the systems, formulations and methods of the present invention.

In another embodiment, delivery of antiviral agents such as acyclovir, trifluridine, idoxuridine, penciclovir, famciclovir, cidofovir, gancyclovir, valacyclovir, podofilox, podophyllotoxin, ribavirin, abacavir, delavirdine, didanosine, efavirenz, lamivudine, nevirapine, stavudine, zalcitabine, zidovudine, amprenavir, indinavir, nelfinavir, ritonavir, saquinavir, amantadine, interferon, oseltamivir, ribavirin, rimantadine, zanamivir, and combinations thereof. Antiviral treatment could be used to treat both localized and systemic viral infections.

A further embodiment involves the peel-forming formulations for the delivery of topically and systemically targeted anti-infectants such as antibiotics.

Other drugs that can be used include humectants, emollients, and other skin care compounds.

The window of operable solubility for certain drugs and drug classes are provided below for exemplary purposes, though it should be noted that the specific non-volatile solvent system can affect these ranges to some degree. For example, a local anesthetic agent can have a window of operable solubility is from about 50 µg/g to about 400 mg/g, and preferably from 100 µg/g to 200 mg/g. An antiviral agent can have a window of operable solubility from about 50 µg/g to about 400 mg/g, and preferably from 100 µg/g to 200 mg/g. A non-steroidal anti-inflammatory agent can have a window of operable solubility from about 200 µg/g to about 400 mg/g, and preferably from 1 mg/g to 200 mg/g. Imiquimod can have a window of operable solubility from about 100 µg/g to about 400 mg/g, and preferably from 1 mg/g to 200 mg/g. Testosterone can have a window of operable solubility from about 0.5 mg/g to about 400 mg/g, and preferably from 1 mg/g to 200 mg/g. An alpha-2 agonist can have a window of operable solubility from about 10 µg/g to about 400 mg/g, and preferably from 1 mg/g to 200 mg/g. An antibiotic can have a window of operable solubility from about 10 µg/g to about 400 mg/g, and preferably 1 mg/g to 200 mg/g. Capsaicin can have a window of operable solubility from about 10 µg/g to about 400 mg/g, and preferably from 100 µg/g to 200 mg/g. A retenoid can have a window of operable solubility from about 5 µg/g to about 400 mg/g, and preferably from 100 µg/g to 200 mg/g.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Skin Permeation Methodology

Hairless mouse skin (HMS) was used as the model membrane for the in vitro flux studies described in herein. Freshly separated epidermis removed from the abdomen of a hairless mouse was mounted carefully between the donor and receiver chambers of a Franz diffusion cell. The receiver chamber was filled with pH 7.4 phosphate buffered saline (PBS). The experiment was initiated by placing test formulations (of Examples 2-5) on the stratum corneum (SC) of the skin sample. Franz cells were placed in a heating block maintained at 37° C. and the HMS temperature was maintained at 35° C. At predetermined time intervals, 800 μL aliquots were withdrawn and replaced with fresh PBS solution. Skin flux (μg/cm$^2$/h) was determined from the steady-state slope of a plot of the cumulative amount of permeation versus time. It is to be noted that human cadaver skin was used as the model membrane for the in vitro flux studies described in Example 10. The mounting of the skin and the sampling techniques used were the same as described previously for the HMS studies.

Examples 2-5

Adhesive Peel-Forming Formulations Including Ketoprofen and In Vitro Testing

A stretchable adhesive peelable formulation for transdermal delivery of ketoprofen (which is suitable for delivery via skin on joints and muscles) was prepared which includes saturated amount of ketoprofen in an excipient mixture (more ketoprofen than that can be dissolved in the excipient mixture) to form an adhesive peelable formulation, some of which are prepared in accordance with embodiments of the present invention. The excipient mixture, which was a viscous and transparent fluid, was prepared using the ingredients as shown in Table 1.

TABLE 1

Ketoprofen Peel-forming Formulation Components.

| Ingredients* | Examples | | | |
| --- | --- | --- | --- | --- |
| | 2 | 3 | 4 | 5 |
| PVA (polyvinyl alcohol) | 1 | 2 | 2 | 2 |
| PEG-400 (polyethylene glycol) | 1 | 1 | 0.27 | 1.75 |
| PVP-K90 (polyvinyl pyrrolidone) | 1 | 0 | 0 | 0 |
| Glycerol | 1 | 1 | 1.8 | 0.27 |
| Water | 2.6 | 5.3 | 5.4 | 5.4 |
| Ethanol | 3 | 0 | 0 | 0 |
| Ketoprofen | | | | |

*Ingredients are noted as parts by weight.

Each of the compositions of Examples 2-5 were studied for flux of ketoprofen, as shown in Table 2, as follows:

TABLE 2

Steady-state flux of ketoprofen through hairless mouse skin from various adhesive peelable formulations at 35° C.

| Formulation | Average flux mcg/cm$^2$/h* |
| --- | --- |
| Example 2 | 8 ± 3 |
| Example 3 | 21 ± 6 |
| Example 4 | 3 ± 1 |
| Example 5 | 1 ± 0.4 |

*The flux values represent the mean and SD of three determinations.

The quantity of ketoprofen that permeated across the hairless mouse skin stratum corneum overtime is shown in FIG. 1.

Regarding formulation described in Example 2, ethanol and water formed the volatile solvent system, while a 1:1 mixture of glycerol and PEG 400 formed the non-volatile solvent system. Through experimentation, it was determined that PEG 400 is a better solvent than glycerol for ketoprofen, while glycerol is much more compatible with PVA than PEG 400. The non-volatile solvent system of glycerol and PEG 400, thus, were used together to provide appropriate solubility for the drug, while being reasonably compatible with PVA. In the formulation in Example 2, PVA and PVP act as the peel-forming agents. Further, in this embodiment, glycerol and PEG 400 also serve as plasticizers in the adhesive peelable formulation formed after the evaporation of the volatile solvents. Without the presence of glycerol and PEG 400, a film formed by PVA and PVP alone would have been rigid and non-stretchable. As can be seen from FIG. 1, the linear relationship between the cumulative amount versus time indicates that ketoprofen was delivered at relatively constant rate over 8 hours after evaporation of at least a portion of the volatile solvents.

Regarding the formulation of Example 3, the adhesive peelable formation formed had similar physical properties as that of Formulation 1, though the transdermal flux across hairless mouse skin was higher. This suggests that the peel-forming agent, 1:1 PVA:PVP-K-90 in Example 2 and pure PVA in example 3, have an impact on permeation.

The formulation in Example 4 delivered less ketoprofen than the formulations of Examples 2 or 3. One reason for the difference could be due to the low concentration of PEG 400 (a good solvent for ketoprofen) in the non-volatile solvent system, which may have resulted in lower quantities of dissolved ketoprofen, and thus, lower skin flux. If a therapeutically effective amount of drug is not supported by this low skin flux, then this example illustrates a scenario in which the solubility is lower than the "window of operable solubility."

The formulation of Example 5 delivered much less ketoprofen than the formulations in Examples 2 and 3. One possible reason for the reduced flux is believed to be the reduced permeation driving force caused by the high concentration of PEG 400 in the non-volatile solvent system, which resulted in too high of solubility for ketoprofen, This illustrates a scenario in which the solubility is higher than the "window of operable solubility." Thus, too low of solubility is not the only consideration when trying to achieve skin flux. In this circumstance, the drug was too "comfortable" or too soluble in the non-volatile solvent system to provide effective skin flux. Thus, high solubility of the ketoprofen put the drug outside of a window of operable solubility to be effective.

The only significant difference among the formulations in Examples 3, 4, and 5, respectively is with respect to the non-volatile solvent system, or more specifically, the PEG 400:glycerol weight ratio. These results reflect the impact of the non-volatile solvent system on skin flux and support for the aforementioned principle that the non-volatile solvent system provides solubility of the drug within the window of operable solubility for delivering therapeutically effective amounts of the drug to, into, or through the skin.

Example 6

Adhesive Peelable Formulation Including Lidocaine and In Vitro Testing

A stretchable adhesive peelable formulation for transdermal delivery of lidocaine was prepared which includes saturated amount of lidocaine in an excipient mixture to form an adhesive peelable formulation in accordance with embodiments of the present invention. The peel formulation was prepared from the ingredients as shown in Table 3.

TABLE 3

Lidocaine Peel-forming Formulation Components.

| Ingredients* | Example 6 |
|---|---|
| PVA | 1 |
| Eudgragit E-100** | 1 |
| PVP-K90 | 0.5 |
| Glycerol | 0.75 |
| PEG-400 | 0.75 |
| Water | 2 |
| Ethanol | 2 |
| Lidocaine | |

*Ingredients are noted as parts by weight.
**from Rohm & Haas.

TABLE 4

Steady-state Flux of Lidocaine through Hairless Mouse Skin from Various Adhesive Peel-forming Formulations at 35° C.

| Formulation | Average flux mcg/cm$^2$/h* |
|---|---|
| Example 6 | 47 ± 3 |

Figure 2:
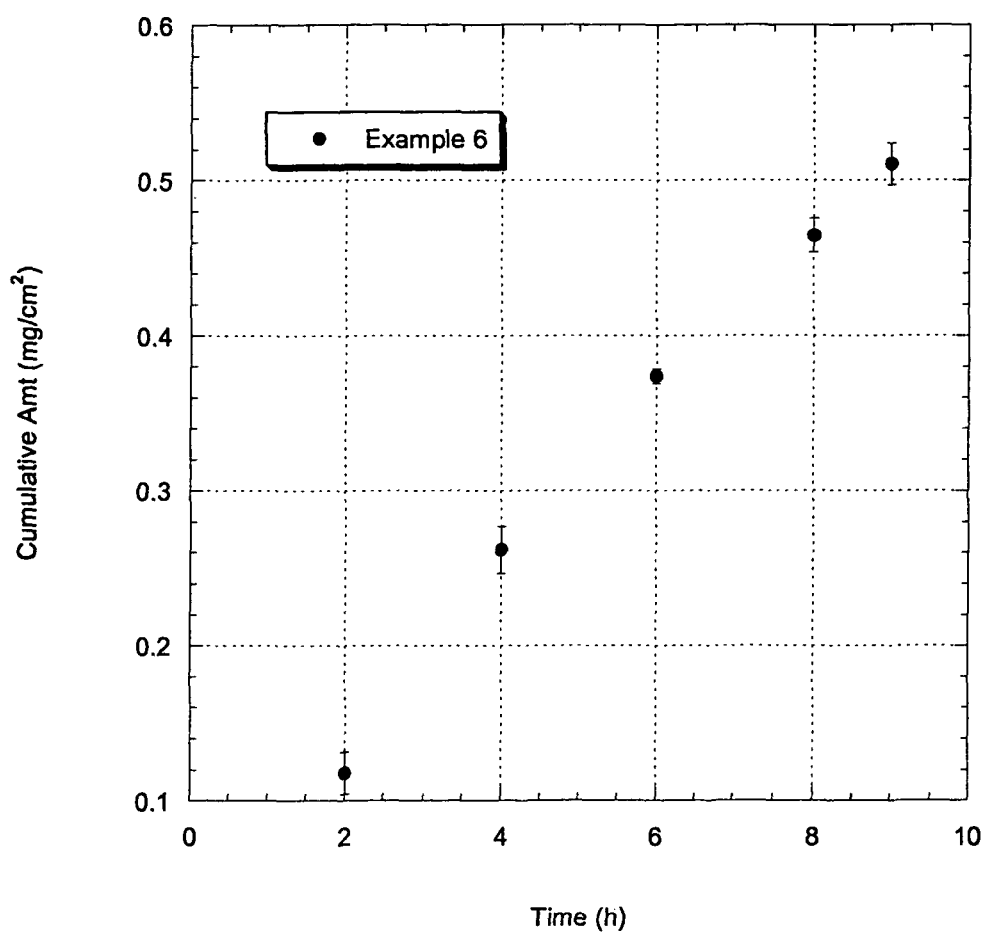

The quantity of lidocaine that permeated across the hairless mouse skin stratum corneum over time is shown in FIG. 2.

The adhesive peelable formulation of lidocaine formulation in the present example had similar physical properties to the formulations in Examples 2-5. The transdermal flux across hairless mouse skin was acceptable and steady-state delivery was maintained over 8 hours.

Example 7

Ropivacaine Flux Using Non-Volatile Solvents

Ropivacaine base flux across hairless mouse skin was determined in several saturated non-volatile solvents as described in Example 1.

TABLE 5

Steady-state Flux Values of Ropivacaine through Hairless Mouse Skin from Saturated Non-volatile Solvent Systems at 35° C.

| Non-Volatile Solvent | Average flux mcg/cm$^2$/h* |
|---|---|
| ISA (isostearic acid) | 11 ± 2 |
| Glycerin | 1.2 ± 0.7 |
| Tween 20 | 2.4 ± 0.1 |
| Mineral Oil | 8.9 ± 0.6 |
| Span 20 | 26 ± 8 |

*The flux values represent the mean and SD of three determinations

It is estimated that for treating skin neuropathic pain, the flux needs to be above 10 μg/cm$^2$/h. The range in ropivacaine flux values from various non-volatile solvents illustrates that some solvents have solubilities that are within the window of operable solubility.

Examples 8-9

Adhesive Peelable Formulations with Ropivacaine

A stretchable adhesive peelable formulation for transdermal delivery of ropivacaine was prepared which includes a specified amount of ropivacaine in an excipient mixture to form an adhesive peelable formulation in accordance with embodiments of the present invention. The peel formulations contained the following components:

TABLE 6

Ropivacaine Peelable Formulation Ingredients.

| | Examples | |
|---|---|---|
| Ingredients* | 8 | 9 |
| Eudragit RL-100 | 1 | 1 |
| Ethanol | 0.6 | 0.6 |
| ISA (isostearic acid) | 0.34 | 0.34 |
| PG (propylene glycol) | 0.2 | 0.1 |
| Trolamine | 0.1 | 0.1 |
| Glycerol | 0.2 | 0.3 |
| Ropivacaine | 0.085 | 0.085 |

* Ingredients are noted as parts by weight.

These formulations were applied to HMS skin as described in Example 1, and the ropivacaine flux was measured. A summary of the results from in vitro flux studies carried out with the formulations in Examples 8 and 9 is listed in Table 7.

TABLE 7

Steady-state Flux of Ropivacaine through Hairless Mouse Skin from Various Adhesive Peelable Formulations at 35° C.

| Formulation | Average flux mcg/cm$^2$/h* |
|---|---|
| Example 8 | 36 ± 5 |
| Example 9 | 32 ± 2 |

*The flux values represent the mean and SD of three determinations

Figure 3:
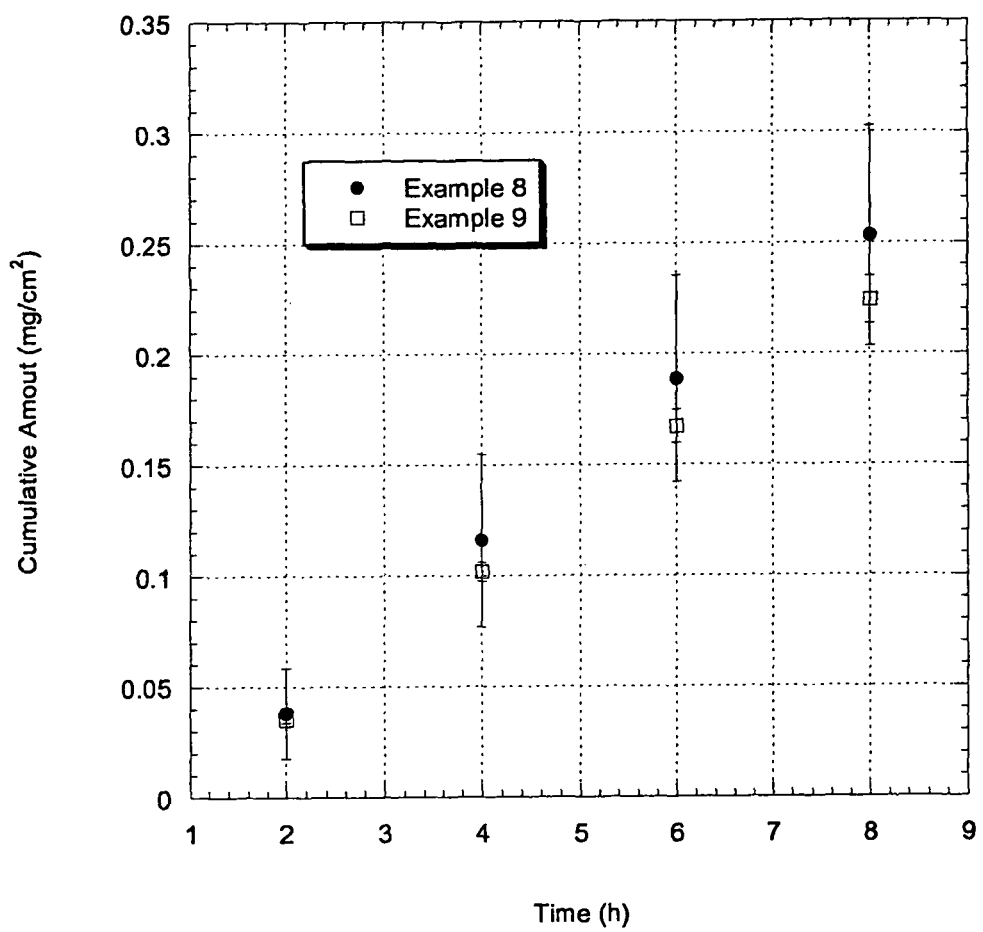

The quantity of ropivacaine that permeated across the hairless mouse skin as a function of time is shown in FIG. 3. Regarding the formulation described in Examples 8 and 9, ethanol was used as the volatile solvent, and the ISA, glycerol, and PG mixture was used as the non-volatile solvent system. Through experimentation, it was determined that ISA and propylene glycol used together to provide the appropriate solubility for the drug, while being compatible with the Eudragit RL-100 film former. Further, in this embodiment, glycerol serves as a plasticizer in the peelable formulation after the ethanol (volatile solvent) has evaporated. The presence of trolamine as a pH adjuster provides solubility of the drug within the window of operable solubility for delivering therapeutically effective amounts of the drug into the skin. The linearity of the cumulative amount versus time curve indicates that ropivacaine was delivered at a relatively constant rate for 8 hours.

Example 10

Adhesive Peel-Forming Formulation Including Diclofenac

A stretchable adhesive peelable formulation for transdermal delivery of diclofenac was prepared which includes saturated amount of diclofenac in an excipient mixture to form an adhesive peelable formulation in accordance with embodiments of the present invention. The peel-forming formulation contained the following components:

TABLE 8

Diclofenac Peelable Formulation Ingredients.

| Ingredients* | Example 10 |
|---|---|
| PVA | 1 |
| Water | 1.5 |
| Eudragit E-100 | 1 |
| Ethanol | 1 |
| Span 20 | 0.6 |

*Ingredients are noted as parts by weight.

Figure 4:
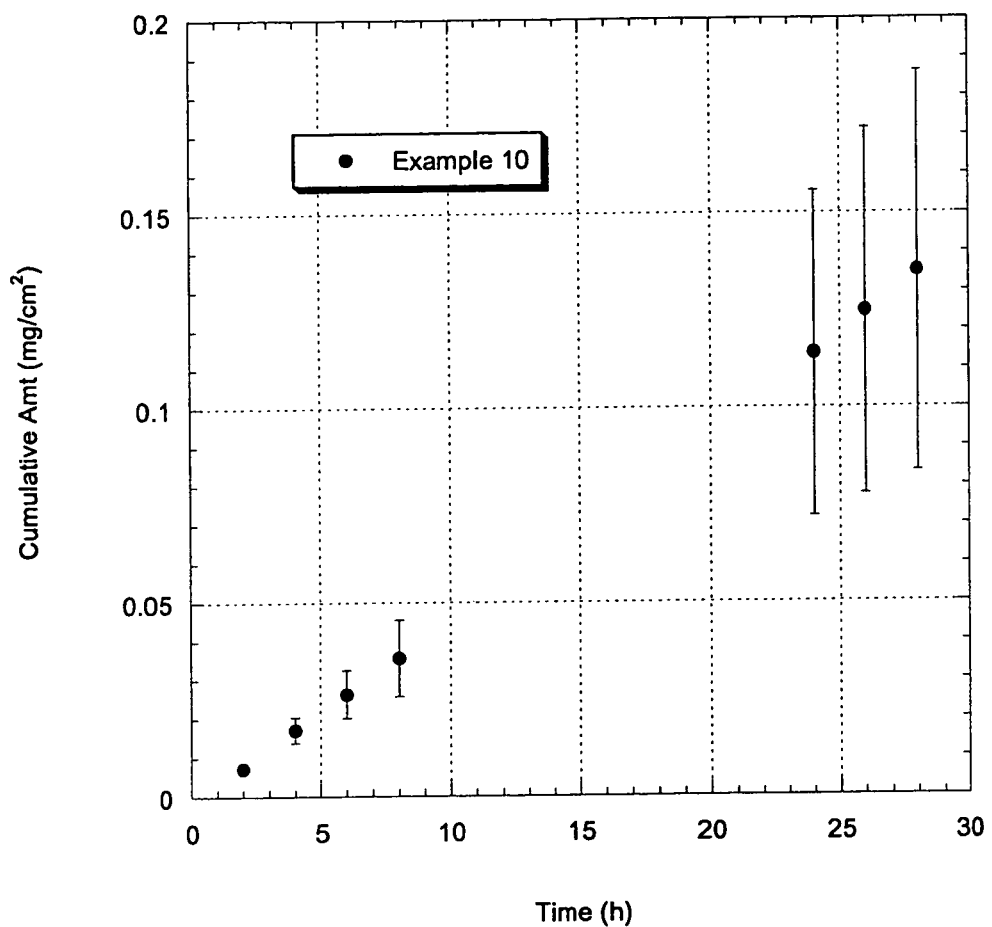

This formulation was applied to a human cadaver skin sample, and the flux across the skin was measured using the method using the method described in Example 1, and was found to be 5±2 µg/cm²/h. The quantity of diclofenac that permeated across the human epidermal membrane over time is shown in FIG. 4. The adhesive peelable formulation of the diclofenac formulation had similar physical properties to the formulations in Example 2-6, and 8 and 9. The transdermal flux across human skin for 30 hours was acceptable.

Example 11

Adhesive Peelable Formulation Flexibility

A formulation similar to the formulation in Example 2 composition (with no ketoprofen) was applied onto a human skin surface at an elbow joint and a finger joint, resulting in a thin, transparent, flexible, and stretchable film. After a few minutes of evaporation of the volatile solvents (ethanol and water), a solidified peelable layer that was peelable was formed. The stretchable film had good adhesion to the skin and did not separate from the skin on joints when bent, and could easily be peeled away from the skin.

Example 12

Non-Volatile Solvent System and Peel-Forming Agent Compatibility

The effect of solubility on permeation, compatibility between the non-volatile solvent system and the peel-forming agent is shown in this example. Ropivacaine base solubility in isostearic acid (ISA) was experimentally determined to be slightly above 1:4, meaning 1 gram ropivacaine base can completely dissolve in 4 gram isostearic acid. In one experiment, two solutions were made: Solution A included 1 part ropivacaine base and 4 parts isostearic acid. Solution B included 1 part ropivacaine base, 4 parts isostearic acid, and 1 part trolamine. (all parts are in weight). All ropivacaine in Solution A was dissolved, but only a portion of ropivacaine in solution B was dissolved. The transdermal flux across hairless mouse skin generated by the solutions was measured by a typical Franz Cell system, with the following results:

TABLE 9

Flux Across Hairless Mouse Skin, in vitro, in $\mu g/hr/cm^2$

| | Cell 1 | Cell 2 | Cell 3 | Average |
|---|---|---|---|---|
| Solution A | 13.1 | 9.9 | 9.1 | 10.7 |
| Solution B | 43.2 | 35.0 | 50.0 | 42.7 |

As can be seen, the flux generated by Solution B is about 4 times that of Solution A. These results demonstrate that reduction of ropivacaine solubility in isostearic acid (the non-volatile solvent system) by the addition of trolamine significantly increased the transdermal flux. However, the attempt to incorporate this system into a poly vinyl alcohol (PVA) based peel formulation failed because the PVA in the formulation acted as a strong pH buffer that inhibited the effect of trolamine. Addition of more trolamine, in attempt to over-power the pH buffer capacity of PVA, caused the loss of the desired peel-forming property of PVA. When PVA was replaced by another peel-forming agent, Eudragit RL 100 (Rohm & Haas), the effect of trolamine was not inhibited and formulations capable of generating fluxes around 30 $\mu g/hr/cm^2$ were obtained. This demonstrates the benefits of compatibility between the non-volatile solvent system and the peel-forming agent.

Example 13

Adhesive Peelable Formulation with Ropivacaine

A stretchable adhesive peelable formulation for transdermal delivery of ropivacaine (which is suitable for delivery via skin on joints and muscles) was prepared from the following ingredients:

TABLE 10

Ropivacaine Peel-forming Formulation Components

| Ingredients* | Example 13 |
|---|---|
| Ropivacaine HCl | 0.096 |
| Eudragit RL-100 | 1.0 |
| Ethanol | 0.7 |
| Isostearic Acid | 0.34 |
| Glycerol | 0.3 |
| Propylene Glycol | 0.1 |
| Trolamine | 0.15 |

*Ingredients are noted as parts by weight.

The ingredients listed above were combined according to the following procedure. The Eudragit RL-100 and ethanol were combined in a glass jar and heated to about 60° C. until the Eudragit RL-100 was completely dissolved. Once the Eudragit solution cooled to room temperature, the appropriate amount of ropivacaine HCl was added and mixed thoroughly for 1 minute. To this solution, isosteric acid (ISA) was added and the mixture was stirred vigorously for 2-3 minutes. One hour later, the solutions was vigorously mixed again for 2-3 minutes. To this solution, glycerol, propylene glycol, and trolamine were added in sequential order. After addition of each ingredient the solution was stirred for 1 minute.

Example 14

Ropivacaine Flux

The formulation prepared in accordance with Example 13 was applied to HMS as described in Example 1, and the ropivacaine flux was measured. A summary of the results is listed in Table 11, as follows:

TABLE 11

Steady-state Flux of Ropivacaine through Hairless Mouse Skin from Various Adhesive Peelable Formulations at 35° C.

| Formulation | Average flux mcg/cm²/h* |
|---|---|
| Example 13 | 43 ± 4 |

*The flux values represent the mean and SD of three determinations

The ropivacaine peel formulations prepared in accordance with Example 13 possessed acceptable application properties, e.g., ease of removal of peel from the sample tube, ease of spreading on intended skin application site, etc., and formed a solidified film in 2-3 minutes. The solidified peelable layer becomes more easily peelable in 2 hours, and the peel remains affixed to the skin surface without any unintended removal of the peel for at least 12 hours. At the end of intended use, the peel is easily removed in one continuous piece.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. An adhesive peel-forming formulation for dermal delivery of a drug, comprising:
    a) a drug, wherein the drug comprises less than 10 wt % of the formulation;
    b) a solvent vehicle, comprising:
        i) a volatile solvent system comprising one or more volatile solvent, and
        ii) a non-volatile solvent system comprising one or more non-volatile solvent, wherein the non-volatile solvent system has a solubility with respect to the drug that is within a window of operable solubility such that the drug is deliverable at therapeutically effective rates over a sustained period of time, and wherein the non-volatile solvent system comprises greater than 20 wt % of the formulation; and
    c) a peel-forming agent, wherein the peel-forming agent comprises 20.8 wt % to 40.9 wt % of the formulation excluding the drug,
    wherein the formulation has a viscosity suitable for application ranging from 1,000 cPs to 1,000,000 cPs, and adhesion to a skin surface prior to evaporation of the volatile solvent system, wherein the formulation applied to the skin surface forms a coherent and soft solidified peelable layer without a backing after at least partial evaporation of the volatile solvent system, and wherein the drug continues to be delivered after the volatile solvent system is substantially evaporated, and wherein the solidified peelable layer has sufficient tensile strength so that it can be peeled off the skin in one piece or several large pieces.

2. A formulation as in claim 1, wherein the non-volatile solvent system acts as a plasticizer for said peel-forming agent.

3. A formulation as in claim 1, wherein the volatile solvent system comprises water.

4. A formulation as in claim 1, wherein the volatile solvent system comprises at least one solvent more volatile than water, and is selected from the group consisting of ethanol, isopropyl alcohol, ethyl acetate, acetone, mixtures thereof, and mixtures with water thereof.

5. A formulation as in claim 1, wherein the non-volatile solvent system comprises at least two non-volatile solvents admixed together which provide a solubility for the drug that is within the window of operable solubility.

6. A formulation as in claim 1, wherein the non-volatile solvent system comprises one or more solvents selected from the group consisting of glycerol, polyethylene glycol having a weight average molecular weight from 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

7. A formulation as in claim 1, wherein the peel-forming agent is selected from the group consisting of polyvinyl alcohol, polyvinyl pyrrolidone, carrageenan, gelatin, and mixtures thereof.

8. A formulation as in claim 1, wherein the peel-forming agent comprises a member selected from the group consisting of dextrin, guar gum, xanthan gum, polyethylene oxide having a weight average molecular weight greater than about 5,000 Mw, starch, cellulose derivatives, and mixtures thereof.

9. A formulation as in claim 8, wherein the peel-forming agent comprises a cellulose derivative selected from the group consisting of hydroxyethylcellulose, ethylcellulose, carboxymethylcellulose, hydroxypropylcellulose, and mixtures thereof.

10. A formulation as in claim 1, wherein the peel-forming agent is selected from the group consisting of polyvinyl alcohol-polyethylene glycol co-polymers, methacrylic acid-based copolymers, and methacrylate-based copolymers, and mixtures thereof.

11. A formulation as in claim 1, wherein the drug comprises at least two pharmaceutically active agents.

12. A formulation as in claim 1, wherein the peel-forming agent comprises a methyacrylic polymer.

13. A formulation as in claim 1, wherein the peel-forming agent comprises a methyacrylic acid-ethyl acrylate copolymer.

14. A formulation as in claim 1, wherein the peel-forming agent comprises a polyvinyl alcohol-polyethylene glycol copolymer.

15. A formulation as in claim 1, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, and combinations thereof.

16. A formulation as in claim 1, wherein the drug is ketoprofen.

17. A formulation as in claim 1, wherein the drug is a humectant or emollient.

18. A formulation as in claim 1, wherein the drug is a steroid for treating herpes infection.

19. A formulation as in claim 1, wherein the drug is a drug for treating a cold sore.

20. A formulation as in claim 1, wherein the drug is a drug for treating genital warts.

21. A formulation as in claim 1, wherein the drug is a drug for treating muscle skeletal pain.

22. A formulation as in claim 1, wherein the drug is diclofenac.

23. A formulation as in claim 1, wherein the drug is an antifungal drug.

24. A formulation as in claim 23, wherein the antifungal drug is selected from the group of ciclopirox, imidazoles, miconazole, clotrimazole, econazole, ketoconazole, oxiconazole, sulconazole, allylamine derivatives, and combinations thereof.

25. A formulation as in claim 1, wherein the drug is an antiviral drug.

26. A formulation as in claim 25, wherein the antiviral drug is selected from the group of acyclovir, trifluridine, idoxuridine, penciclovir, famciclovir, cidofovir, gancyclovir, valacyclovir, podofilox, podophyllotoxin, ribavirin, abacavir, delavirdine, didanosine, efavirenz, lamivudine, nevirapine, stavudine, zalcitabine, zidovudine, amprenavir, indinavir, nelfinavir, ritonavir, saquinavir, amantadine, interferon, oseltamivir, rimantadine, zanamivir, and combinations thereof.

27. A formulation as in claim 1, wherein the drug is an anti-infective.

28. A formulation as in claim 1, wherein the solidified peelable layer is sufficiently flexible and adhesive to the skin such that when applied to the skin at a human joint, the solidified peelable layer will remain substantially intact on the skin upon bending of the joint.

29. A formulation as in claim 1, wherein the solidified peelable layer delivers the drug at a substantially constant rate for at least 2 hours.

30. A formulation as in claim 1, wherein the solidified peelable layer delivers the drug at a substantially constant rate for at least 4 hours.

31. A formulation as in claim 1, wherein the solidified peelable layer delivers the drug at a substantially constant rate for at least 8 hours.

32. A formulation as in claim 1, wherein the solidified peelable layer delivers the drug at a substantially constant rate for at least 12 hours.

33. A formulation as in claim 1, wherein the peel-forming agent is dispersed or solvated in the solvent vehicle.

34. A formulation as in claim 1, wherein the window of operable solubility is predetermined.

35. A formulation as in claim 1, wherein the weight ratio of the non-volatile solvent system to the peel-forming agent is from 0.2:1 to 1.2:1.

36. A formulation as in claim 1, wherein the volatile solvent system causes human skin irritation and at least one non-volatile solvent of said non-volatile solvent system reduces the skin irritation.

37. A formulation as in claim 36, wherein the non-volatile solvent that reduces skin irritation is selected from the group consisting of glycerin, propylene glycol, and honey.

38. A formulation as in claim 1, wherein the solidified peelable layer is formed within 15 minutes of application to the skin surface under standard skin and ambient conditions.

39. A formulation as in claim 1, wherein the solidified peelable layer is formed within 4 minutes of the application to the skin surface under standard skin and ambient conditions.

40. A formulation as in claim 1, wherein the weight percentage of the volatile solvent system is from 2 wt % to 50 wt %.

41. A formulation as in claim 1, wherein the weight percentage of the volatile solvent system is from 4 wt % to 30 wt %.

42. A formulation as in claim 1, wherein the non-volatile solvent system comprises at least two non-volatile solvents, and at least one of the non-volatile solvents improves the compatibility of the non-volatile solvent system with the peel-forming agent.

43. A formulation as in claim 1, wherein the drug is a local anesthetic agent and the window of operable solubility is from about 50 µg/g to about 400 mg/g.

44. A formulation as in claim 1, wherein the drug is an antiviral agent and the window of operable solubility is from about 50 µg/g to about 400 mg/g.

45. A formulation as in claim 1, wherein the drug is a non-steroidal anti-inflammatory agent and the window of operable solubility is from 200 µg/g to 400 mg/g.

46. A formulation as in claim 1, wherein the drug is imiquimod and the window of operable solubility is from about 100 µg/g to about 400 mg/g.

47. A formulation as in claim 1, wherein the drug is testosterone and the window of operable solubility is from about 0.5 mg/g to about 400 mg/g.

48. A formulation as in claim 1, wherein the drug is an alpha-2 agonist and the window of operable solubility is from about 10 µg/g to about 400 mg/g.

49. A formulation as in claim 1, wherein the drug is an antibiotic and the window of operable solubility is from about 10 µg/g to about 400 mg/g.

50. A formulation as in claim 1, wherein the drug is capsaicin and the window of operable solubility is from about 10 µg/g to about 400 mg/g.

51. A formulation as in claim 1, wherein the drug is a retinoid and the window of operable solubility is from about 5 µg/g to about 400 mg/g.

52. A method of dermally delivering a drug, comprising:
 a) applying the adhesive peel-forming formulation of claim 1 to the skin surface of a subject; and
 b) dermally delivering the drug from the solidified peelable layer to the subject at therapeutically effective rates over a sustained period of time.

53. A method as in claim 52, wherein the step of applying comprises applying the adhesive peel-forming formulation at a thickness from about 0.01 mm to about 2 mm.

54. A method as in claim 53, wherein the thickness is from about 0.05 mm to about 1 mm.

55. A method as in claim 52, wherein the non-volatile solvent system comprises at least two non-volatile solvents admixed together to form a mixture, said mixture providing a solubility for the drug that is within the window of operable solubility.

56. A method as in claim 52, wherein the non-volatile solvent system comprises one or more solvent selected from the group consisting of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

57. A method as in claim 52, wherein the peel-forming agent is selected from the group consisting of polyvinyl alcohol, polyvinyl pyrrolidone, carrageenan, gelatin, and mixtures thereof.

58. A method as in claim 52, wherein the peel-forming agent comprises a member selected from the group consisting of dextrin, guar gum, xanthan gum, polyethylene oxide having a weight average molecular weight greater than about 5,000 Mw, starch, cellulose derivatives, and mixtures thereof.

59. A method as in claim 58, wherein the peel-forming agent comprises a cellulose derivative selected from the group consisting of hydroxyethylcellulose, ethylcellulose, carboxymethylcellulose, hydroxypropylcellulose, and mixtures thereof.

60. A method as in claim 52, wherein the peel-forming agent is selected from the group consisting of polyvinyl alcohol-polyethylene glycol co-polymers, methacrylic acid-based copolymers, and methacrylate-based copolymers, and mixtures thereof.

61. A method as in claim 52, wherein the drug comprises at least two pharmaceutically active agents.

62. A method as in claim 52, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, and mixtures thereof.

63. A method as in claim 52, wherein the drug is a steroid for treating herpes infection.

64. A method as in claim 52, wherein the drug is for treating a cold sore.

65. A method as in claim 52, wherein the drug is a drug for treating genital warts.

66. A method as in claim 52, wherein the drug is for treating muscle skeletal pain.

67. A method as in claim 52, wherein the drug is an antifungal drug selected from the group consisting of ciclopirox, imidazoles, miconazole, clotrimazole, econazole, ketoconazole, oxiconazole, sulconazole, allylamine derivatives, and combinations thereof.

68. A method as in claim 52, wherein the drug is an antiviral drug selected from the group consisting of acyclovir, trifluridine, idoxuridine, penciclovir, famciclovir, cidofovir, gancyclovir, valacyclovir, podofilox, podophyllotoxin, ribavirin, abacavir, delavirdine, didanosine, efavirenz, lamivudine, nevirapine, stavudine, zalcitabine, zidovudine, amprenavir, indinavir, nelfinavir, ritonavir, saquinavir, amantadine, interferon, oseltamivir, rimantadine, zanamivir, and combinations thereof.

69. A method as in claim 52, wherein the solidified peelable layer is sufficiently flexible and adhesive to the skin such that when applied to the skin at a human joint, the solidified peelable layer will remain substantially intact on the skin upon bending of the joint.

70. A method as in claim 52, wherein the solidified peelable layer delivers the drug at a substantially constant rate for at least 2 hours.

71. A method as in claim 52, wherein the solidified peelable layer delivers the drug at a substantially constant rate for at least 4 hours.

72. A method as in claim 52, wherein the solidified peelable layer delivers the drug at a substantially constant rate for at least 8 hours.

73. A method as in claim 52, wherein the solidified peelable layer delivers the drug at a substantially constant rate for at least 12 hours.

74. A method as in claim 52, wherein the weight ratio of the non-volatile solvent system to the peel-forming agent is from about 0.01:1 to about 2:1.

75. A method as in claim 52, wherein the weight ratio of the non-volatile solvent system to the peel-forming agent is from about 0.2:1 to about 1.2:1.

76. A method as in claim 52, wherein the solidified peelable layer is formed within 15 minutes of the application to the skin surface.

77. A method as in claim 52, wherein the solidified peelable layer is formed within 4 minutes of the application to the skin surface.

78. A method as in claim 52, wherein the step of applying comprises applying the adhesive peelable formulation over an area of the skin surface that is sufficiently large to deliver a therapeutically effective amount of the drug.

79. A method of preparing the adhesive peel-forming formulation of claim 1 for dermal drug delivery, comprising:
   a) selecting the drug, said drug being suitable for dermal delivery;
   b) selecting the non-volatile solvent system, said non-volatile solvent system consisting essentially of one non-volatile solvent that has a solubility with respect to the drug within a window of operable solubility; and
   c) formulating the drug and the non-volatile solvent into an adhesive peel-forming formulation that further comprises at least one peel-forming agent and at least one volatile solvent system.

80. A method as in claim 79, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, antifungal drugs, and combinations thereof.

81. A method as in claim 79, wherein the non-volatile solvent is selected from the group consisting of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

82. A method of preparing the adhesive peel-forming formulation of claim 1 for dermal drug delivery, comprising:
   a) selecting the drug, said drug being suitable for dermal delivery;
   b) forming the non-volatile solvent system by selecting at least two non-volatile solvents according to a ratio of a first non-volatile solvent to a second non-volatile solvent, wherein the ratio positions the solubility of the drug in the non-volatile solvent system within a window of operable solubility; and
   c) formulating the drug and the non-volatile solvent system into an adhesive peel-forming formulation that further comprises at least one peel-forming agent and at least one volatile solvent system.

83. A method as in claim 82, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, and combinations thereof.

84. A method as in claim 82, wherein the non-volatile solvent system comprises a member selected from the group of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

85. A method as in claim 82, wherein at least one of the non-volatile solvents is added to improve non-volatile solvent system compatibility with the peel-forming agent.

86. A solidified peelable layer for delivering a drug formed from the adhesive peel-forming formulation of claim 1,
wherein the non-volatile solvent system provides delivery of the drug at therapeutically effective rates for at least 2 hours,
and wherein said peelable layer can be stretched in at least one direction by 10% without breaking or cracking.

87. A solidified peelable layer as in claim 86, wherein the non-volatile solvent system acts as a plasticizer for the peel-forming agent.

88. A solidified peelable layer as in claim 86, wherein solidified peelable layer is sufficiently adhesive and flexible to remain substantially intact on a skin surface adjacent to a joint or muscle group where regular skin stretching occurs.

89. A solidified peelable layer as in claim 86, wherein the non-volatile solvent system comprises at least two solvents admixed together according to a ratio of a first non-volatile solvent to a second non-volatile solvent, wherein the ratio positions the solubility of the drug within a window of operable solubility with respect to the non-volatile solvent system.

90. A solidified peelable layer as in claim 86, wherein the non-volatile solvent system comprises a member selected from the group of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

91. A solidified peelable layer as in claim 86, wherein the peel-forming agent comprises a member selected from the group consisting of methyacrylic polymer, methyacrylic acid-ethyl acrylate copolymer, polyvinyl alcohol-polyethylene glycol copolymer, polyvinyl alcohol, polyvinyl pyrrolidone, carrageenan, gelatin, dextrin, guar gum, xanthan gum, polyethylene oxide, starch, cellulose derivatives, copolymers of methyl vinyl ether and maleic anhydride, and mixtures thereof.

92. A solidified peelable layer as in claim 86, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, antifungal drugs, and combinations thereof.

93. An adhesive peel-forming formulation as in claim 1 for dermal delivery of the drug,
wherein the solidified peelable layer has a contact surface, said contact surface having a first area dimension, said solidified peelable layer being stretchable such that the first area dimension is capable of being stretched to a second area dimension that is 10% larger than the first area dimension without cracking, breaking, or separating from the skin surface.

94. A formulation as in claim 93, wherein the volatile solvent system comprises a member selected from the group consisting of water, ethanol, isopropyl alcohol, ethyl acetate, acetone, and mixtures thereof.

95. A formulation as in claim 93, wherein the non-volatile solvent system comprises one or more solvents selected from the group consisting of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof.

96. A formulation as in claim 93, wherein the peel-forming agent comprises a member selected from the group consisting of polyvinyl alcohol, polyvinyl pyrrolidone, carrageenan, gelatin, dextrin, guar gum, xanthan gum, polyethylene oxide having a weight average molecular weight greater than about 5,000 Mw, starch, cellulose derivatives, and mixtures thereof.

97. A formulation as in claim 93, wherein the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, antifungal drugs, and combinations thereof.

98. A formulation as in claim 93, wherein the solidified peelable layer is sufficiently flexible and adhesive to the skin such that when applied to the skin at a human joint, the solidified peelable layer will remain substantially intact on the skin upon bending of the joint.

99. A formulation as in claim 93, wherein the weight ratio of the non-volatile solvent system to the peel-forming polymer is from about 0.01:1 to about 2:1.

100. A formulation as in claim 93, wherein the weight ratio of the non-volatile solvent system to the peel-forming polymer is from about 0.2:1 to about 1.2:1.

101. A formulation as in claim 93, wherein the solidified peelable layer is formed within 15 minutes of the application to the skin surface under normal skin and ambient conditions.

102. A formulation as in claim 93, wherein the solidified peelable layer is formed within 4 minutes of the application to the skin surface.

103. An adhesive peel-forming formulation as in claim 1 for dermal delivery of the drug, wherein:
a) the drug is selected from the group consisting of non-steroidal anti-inflammatory drugs (NSAIDs), COX-2 selective NSAIDs, COX-3 selective NSAIDs, local anesthetics, steroids, antibiotics, retinoids, clonidine, peroxides, retinol, salicylic acid, imiquimod, humectants, emollients, antiviral drugs, antifungal drugs, and combinations thereof;
b) the solvent vehicle comprises:
i) the volatile solvent system, wherein the volatile solvent system comprises one or more volatile solvent selected from the group of water, ethanol, isopropyl alcohol, ethyl acetate, acetone, mixtures thereof, and ii) the non-volatile solvent system, wherein the non-volatile solvent system has a solubility with respect to the drug that is within a window of operable solubility such that the drug is deliverable at therapeutically effective rates over a sustained period of time; and said one or more non-volatile solvent comprises a non-volatile solvent selected from the group consisting of glycerol, polyethylene glycol having a weight average molecular weight from about 200 MW to 800 MW, mineral oil, petrolatum, castor oil, n-methyl pyrrolidone, vegetable oil, honey, oleyl alcohol, dipropylene glycol, polyoxyethylene derivative of sorbitan esters, saturated polyglycolyzed $C_8$ to $C_{10}$ glycerides, polyoxyethylated fatty acid glycerides, dimethylsulfoxide, fatty alcohol, isopropyl myristate, ethyl oleate, essential oils, oleic acid, isostearic acid, fatty acids, and mixtures thereof; and c) the peel-forming agent comprises a peel-forming agent selected from the group consisting of polyvinyl alcohol, polyvinyl pyrrolidone, carrageenan, gelatin, dextrin, guar gum, xanthan gum, polyethylene oxide, hydroxyethylcellulose, ethylcellulose, carboxymethylcellulose, hydroxypropylcellulose, copolymers of methyl vinyl ether and maleic anhydride, polyvinyl alcohol-polyethylene glycol co-polymers, methacrylic acid-based copolymers, methacrylate-based copolymers, and mixtures thereof;

wherein the formulation has a drying time of 5 minutes or shorter under standard skin and ambient conditions, wherein the weight ratio of the non-volatile solvent system to the peel-forming polymer is from about 0.2:1 to about 1.2:1, and wherein the solidified peelable layer can be stretched in at least one direction by 10% without cracking, breaking, or separating from the skin.

104. A formulation as in claim 1, wherein the weight ratio of the non-volatile solvent system to the peel-forming agent is from 0.01:1 to 2:1.

105. A formulation as in claim 1, wherein the total drug concentration is up to 6 wt %.

106. A formulation as in claim 105, wherein the non-volatile solvent system is present in the formulation at from 21.4 wt % to 34.4 wt % excluding the total drug concentration.

107. A formulation as in claim 106, wherein there are at least two non-volatile solvents present in the non-volatile solvent system.

108. A formulation as in claim 105, wherein there are at least two non-volatile solvents present in the non-volatile solvent system.

109. A formulation as in claim 6, wherein the non-volatile solvent system comprises eugenol or rose oil.

110. A formulation as in claim 6, wherein the non-volatile solvent system comprises a medium chain fatty acid.

111. A formulation as in claim 10, wherein the peel-forming agent comprises a poly(methacrylic acid) copolymer, a methylmethacrylate copolymer, a methyacrylic acid-ethyl acrylate copolymer, or mixtures thereof.

112. A formulation as in claim 1, wherein the peel-forming agent comprises copolymers of methyl vinyl ether and maleic anhydride.

113. A formulation as in claim 24, wherein the antifungal drug comprises butenafine, naftifine, and terbinafine, or mixtures thereof.

114. A formulation as in claim 1, wherein the drug is lidocaine, bupivacaine, ropivacaine, tetracaine, and mixtures thereof.

115. A formulation as in claim 1, wherein the drug is dexamethasone.

* * * * *